(12) United States Patent
Wissman et al.

(10) Patent No.: US 7,425,195 B2
(45) Date of Patent: Sep. 16, 2008

(54) RADIATION SHIELDING DEVICE

(75) Inventors: Lawrence Y. Wissman, Santa Barbara, CA (US); Jerry R. Barber, Ventura, CA (US)

(73) Assignee: Core Oncology, Inc., Mercer Island, WA (US)

( * ) Notice: Subject to any disclaimer, the term of this patent is extended or adjusted under 35 U.S.C. 154(b) by 334 days.

(21) Appl. No.: 10/918,846

(22) Filed: Aug. 13, 2004

(65) Prior Publication Data
US 2006/0063960 A1 Mar. 23, 2006

(51) Int. Cl.
*A61M 36/00* (2006.01)
(52) U.S. Cl. .......................................................... 600/7
(58) Field of Classification Search ................. 600/1–8; 250/455.11, 453.11, 505.1, 506.1, 507.1; 128/897, 898
See application file for complete search history.

(56) References Cited

U.S. PATENT DOCUMENTS

| | | | | | |
|---|---|---|---|---|---|
| 4,923,088 | A | * | 5/1990 | Tanaka et al. | 220/23.87 |
| 5,460,592 | A | * | 10/1995 | Langton et al. | 600/7 |
| 5,834,788 | A | * | 11/1998 | Fu et al. | 250/506.1 |
| 6,366,633 | B1 | * | 4/2002 | Stezaly et al. | 376/202 |
| 6,989,543 | B2 | * | 1/2006 | Drobnik et al. | 250/455.11 |
| 2003/0144571 | A1 | * | 7/2003 | Mick et al. | 600/7 |

* cited by examiner

*Primary Examiner*—Samuel G Gilbert
(74) *Attorney, Agent, or Firm*—DLA Piper US LLP

(57) ABSTRACT

Radiation shielding devices are provided herein. In particular, the devices provided herein can be adapted to shield radiation emitted by one or more radioactive brachytherapy seeds contained within, for example, a vial or a cartridge.

15 Claims, 16 Drawing Sheets

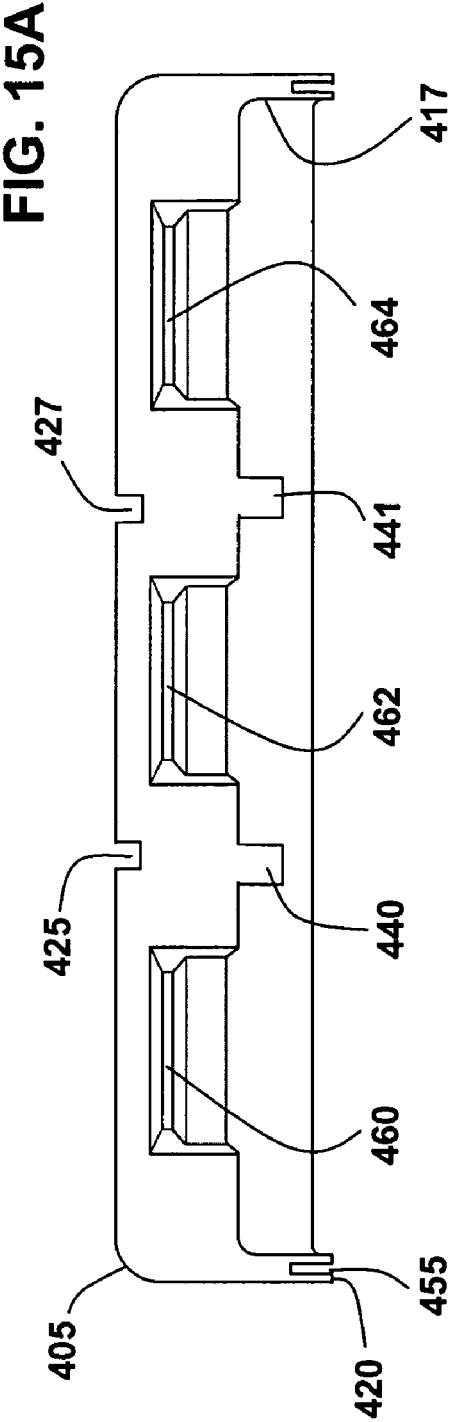
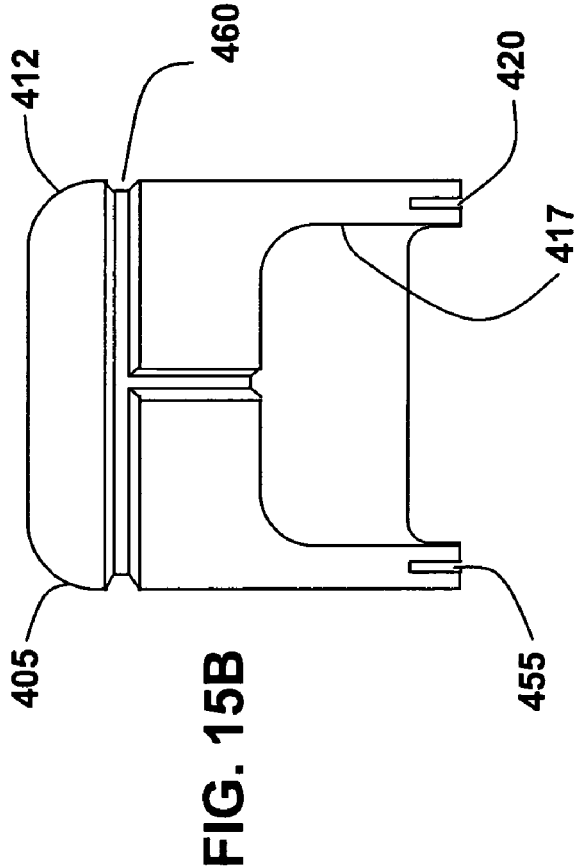
FIG. 15A
FIG. 15B

RADIATION SHIELDING DEVICE

TECHNICAL FIELD

This invention relates to a shielding device for a radiation source, and in particular relates to a shielding device for radioactive brachytherapy seeds.

BACKGROUND

Brachytherapy is a form of cancer treatment in which radiation sources are placed inside a patient's body to irradiate a tumor. In brachytherapy, a surgeon usually implants several radioactive seeds in or around a tumor, thus providing a higher radiation dose to the tumor than would be possible with external beam radiation therapy. Careful placement of the radioactive seeds allows localized and precise irradiation of the tumor.

Radioactive seeds typically are very small (generally about 0.8 mm by 4.5 mm), roughly cylindrical objects containing very small amounts of radioactive material. Two radioactive isotopes commonly used for permanent implants are iodine-125, often used to treat slower growing tumors, and palladium-103, which is preferred when a tumor is fast growing. Other radioactive materials also can be used in implants.

Radioactive seeds for use in brachytherapy procedures typically are carried in and used from small containers such as seed cartridges that can be used with a delivery system (e.g., a brachytherapy applicator such as the Mick applicator). Alternatively, radioactive seeds can be packaged loose in small glass or plastic vials for later assembly into seed cartridges or brachytherapy needles. In either case, the radioactive seeds can be loaded into a seed cartridge and/or a brachytherapy applicator for delivery to the patient.

SUMMARY

Holding devices (e.g., vials and cartridges) containing radioactive brachytherapy seeds can be shipped, carried, and stored in shielding devices made of or containing absorbing elements, compounds, and admixtures that can both absorb the radiation and shield the surrounding area from the radiation. These shielding devices can be large enough to contain several seed holding devices, and often are made of lead, stainless steel, aluminum, or other radiation shielding materials. Such shielding devices, however, can be heavy, bulky, difficult to handle, and deficient in radiation shielding, resulting in some exposure of a user (e.g., a clinician) to radiation from the seeds.

The invention provides efficient radiation shielding devices that are light, convenient, easily produced, and inexpensive. These devices can be used for shipping, storage, and processing of radiation sources such as brachytherapy seeds. Use of the devices can facilitate handling of radioactive seeds, and can result in reduced radiation exposure and improved safety. In addition, because the devices provided herein are relatively light, they can be less expensive to ship and also simpler and quicker to use. For example, sterilization (e.g., autoclaving) times can be reduced, since such times are influenced by the mass of the object to be sterilized. Further, the devices can be reused or recycled.

In one aspect, the invention features a brachytherapy seed holding device and a radiation shielding device configured to engage the seed holding device, wherein (a) the seed holding device has a radioactive seed contained within a compartment of the seed holding device; (b) the radiation shielding device includes a member having an interior surface and an exterior surface; (c) the member extends over at least a portion of the compartment when the shielding device is engaged with the seed holding device; and (d) the member defines an opening extending between the interior surface and the exterior surface such that there is no direct line of sight from the exterior of the member through the opening to the compartment when the shielding device is engaged with the seed holding device. The shielding device can be between 25 mm and 90 mm in length. The shielding device can be between 6 mm and 16 mm in width. The shielding device can have an inner diameter between 4 mm and 6 mm (e.g., about 5 mm). The shielding device can have an outer diameter between 25 mm and 35 mm (e.g., about 30 mm). The seed holding device can define an external screw thread, the interior surface of the member can define an internal screw thread, and the internal screw thread can be configured to engage the external screw thread. The shielding device can be adapted such that there is no direct line of sight from the exterior of the member through the opening to the compartment when the shielding device is fully engaged with the seed holding device. The shielding device can be adapted such that there is no direct line of sight from the exterior of the member through the opening to the compartment when the shielding device is partially engaged with the seed holding device.

The shielding device can have an inner member and an outer member. The inner and outer members can be adapted to engage one another through a snap fit, a bayonet fit, or a screw fit. One of the inner and outer members can define a protrusion, the other of the inner and outer members can define a recess adapted to receive the protrusion, and the outer member can be configured to slidably receive the inner member when the protrusion is inserted into the recess. The inner member can have a cantilever spring. The cantilever spring can define a protrusion, and the outer member can define a groove adapted to engage the protrusion. The inner member and the outer member each can have an exterior and an interior, wherein the inner member defines a first opening and the outer member defines a second opening, and wherein when the inner and outer members are engaged with one another, there is no direct line of sight from the exterior of the outer member through the opening to the interior of the inner member. The inner member can define an extension configured to shield a window in the compartment.

The shielding device can have a top member and a bottom member. The top and bottom members can each define a screw thread, wherein the screw threads are adapted to engage one another. The top and bottom members can be adapted to engage each other through a snap fit, a bayonet fit, or a screw fit. The shielding device can have a first outer member, a first inner member, and a second member.

The shielding device can be configured to shield the entirety of the seed holding device. The shielding device can contain metal, a thermoplastic or thermoset material, or a filled thermoplastic or thermoset material (e.g., a thermoplastic or thermoset material filled with antimony, tungsten, barium sulfate, a bismuth compound, titanium dioxide, lead, or steel).

In another aspect, the invention features a radiation shielding device configured to engage a brachytherapy seed holding device, wherein: (a) the shielding device includes a member having an interior surface and an exterior surface; (b) the seed holding device defines an external screw thread; (c) the interior surface of the member defines an internal screw thread configured to engage the external screw thread; (d) the seed holding device has a compartment configured to retain a brachytherapy seed; (e) the member extends over at least a portion of the compartment when the internal screw thread is engaged with the external screw thread; and (f) the member defines an opening extending between the interior surface and the exterior surface such that there is no direct line of sight from the exterior of the member through the opening to the compartment when the shielding device is engaged with the seed holding device. The shielding device can be between 25 mm and 90 mm in length. The shielding device can be between 6 mm and 16 mm in width. The shielding device can have an inner diameter between 4 mm and 6 mm (e.g., about 5 mm). The shielding device can have an outer diameter between 25 mm and 35 mm (e.g., about 30 mm). The shielding device can be configured such that there is no direct line of sight from the exterior of the member through the opening to the compartment when the shielding device is fully engaged with the seed holding device. The shielding device can be configured such that there is no direct line of sight from the exterior of the member through the opening to the compartment when the shielding device is partially engaged with the seed holding device.

The shielding device can have an inner member and an outer member. The inner and outer members can be adapted to engage one another through a snap fit, a bayonet fit, or a screw fit. One of the inner and outer members can define a protrusion, the other of the inner and outer members can define a recess adapted to receive the protrusion, and the outer member can be configured to slidably receive the inner member when the protrusion is inserted into the recess. The inner member can have a cantilever spring. The cantilever spring can define a protrusion, and the outer member can define a groove adapted to engage the protrusion. The inner member and the outer member each can have an exterior and an interior, wherein the inner member defines a first opening, wherein the outer member defines a second opening, and wherein when the inner and outer members are engaged with one another, there is no direct line of sight from the exterior of the outer member through the openings to the interior of the inner member. The inner member can define an extension configured to shield a window in the compartment.

The shielding device can have a top member and a bottom member. The top and bottom members each can define a screw thread, wherein the screw threads are adapted to engage one another. The top and bottom members can be adapted to engage each other through a snap fit, a bayonet fit, or a screw fit. The shielding device can have a first outer member, a first inner member, and a second member.

The shielding device can be configured to shield the entirety of the seed holding device. The shielding device can contain metal, a thermoplastic or thermoset material, or a filled thermoplastic or thermoset material (e.g., a thermoplastic or thermoset material filled with antimony, tungsten, barium sulfate, a bismuth compound, titanium dioxide, lead, or steel).

In another aspect, the invention features a radiation shielding device configured to receive a plurality of brachytherapy seeds. The device can have a bottom outer member, a bottom inner member; and a top member, wherein each member has an interior surface and an exterior surface, wherein the bottom inner member has a feature for engaging the bottom outer member, wherein the bottom outer member defines a feature for engaging the top member, and wherein at least one of the members defines an opening between the interior surface and the exterior surface such that there is no direct line of sight from the exterior of the device through the opening to the interior of the device when the bottom inner member is engaged with the bottom outer member and the bottom outer member is engaged with the top member. The bottom inner member can define a fin, the bottom outer member can define a groove, and the fin can be slidably engagable in the groove. The bottom outer member and the top member each can define a screw thread, the screw threads being configured to engage each other. The device can contain a thermoplastic or thermoset material, or a filled thermoplastic or thermoset material (e.g., a thermoplastic or thermoset material filled with antimony, tungsten, barium sulfate, a bismuth compound, titanium dioxide, lead, or steel). The device can be between 25 mm and 90 mm in length. The device can be between 6 mm and 16 mm in width.

In yet another aspect, the invention features a radiation shielding device configured to retain a brachytherapy seed holding device. The shielding device can have: (a) a first member with a first interior surface, a first exterior surface, and a first mating edge, the first mating edge defining a protrusion, and (b) a second member with a second interior surface, a second exterior surface, and a second mating edge, the second mating edge defining a recess adapted to receive the protrusion. The first member can define a first opening extending between the first interior surface and the first exterior surface, such that when the shielding device contains at least a portion of a seed holding device, there is no direct line of sight from the exterior of the first member to the portion of the seed holding device. The second member can define a second opening extending between the second interior surface and the second exterior surface, such that when the shielding device contains a at least a portion of the seed holding device, there is no direct line of sight from the exterior of the second member to the portion of the seed holding device. The first and second exterior surfaces each can define a recess adapted to receive a connector. The first and second interior surfaces each can define a ridge. The shielding device can be between 25 mm and 90 mm in length. The shielding device can be between 6 mm and 16 mm in width. The shielding device can have an inner diameter between 4 mm and 6 mm (e.g., about 5 mm). The shielding device can have an outer diameter between 20 mm and 40 mm (e.g., about 30 mm). The shielding device can contain metal, a thermoplastic or thermoset material, or a filled thermoplastic or thermoset material (e.g., a thermoplastic or thermoset material filled with antimony, tungsten, barium sulfate, a bismuth compound, titanium dioxide, lead, or steel).

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 15A is a diagram showing a longitudinal cross-section of a second embodiment of the first piece shown in FIG. 13. FIG. 15B is a lateral cross-sectional view of the embodiment shown in FIG. 15A.

Like reference symbols in the various drawings indicate like elements.

DETAILED DESCRIPTION

Figure 1:
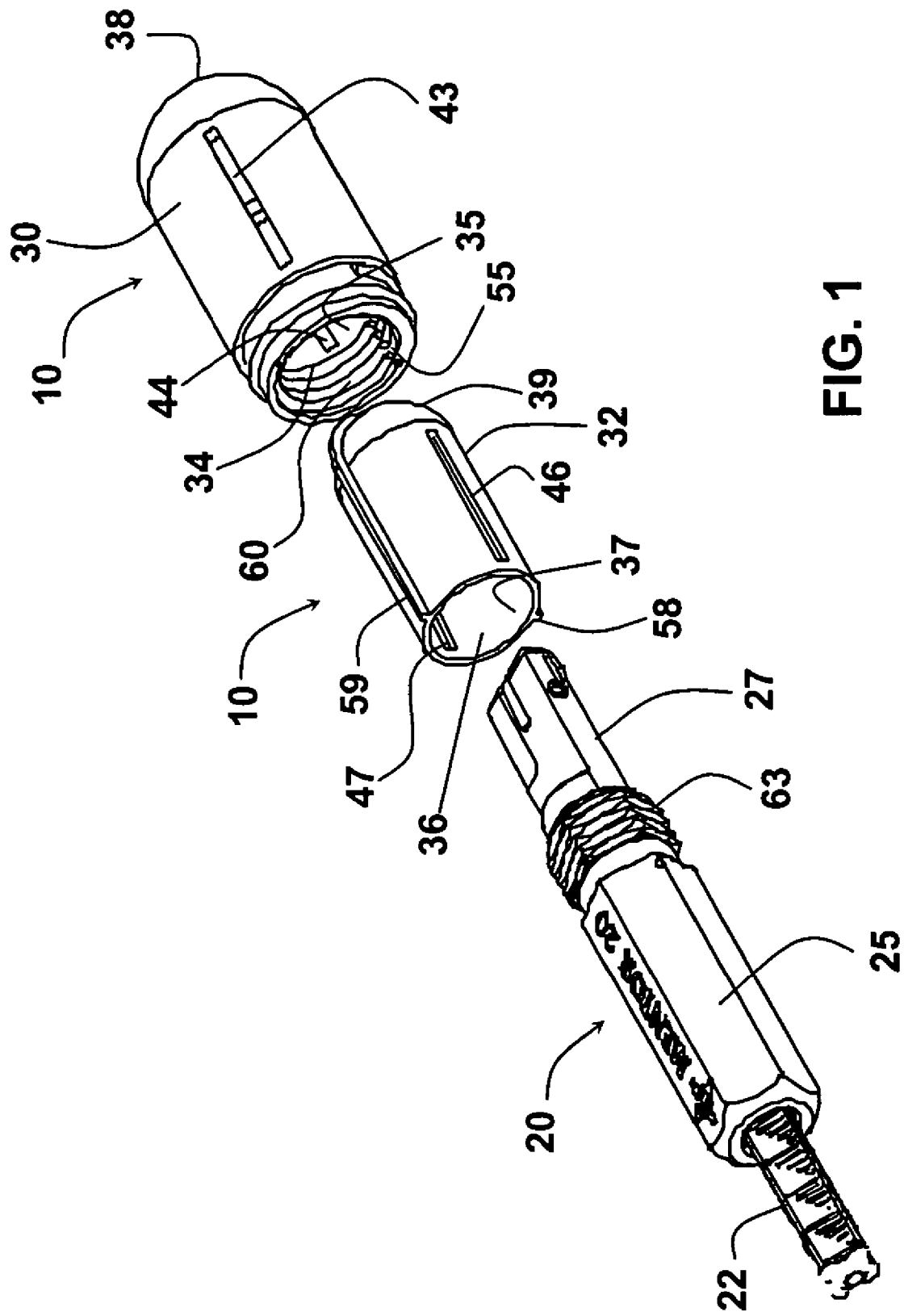
FIG. 1 is a diagram of a seed cartridge and a two-part radiation shielding device.

The invention provides efficient radiation shielding devices that are light, convenient, easily produced, and inexpensive. These devices can be used for shipping, storage, and processing (e.g., sterilization) of radiation sources such as brachytherapy seeds. Use of the devices can facilitate handling of radioactive seeds, and can result in reduced radiation exposure, reduced sterilization time, reduced shipping costs, and improved safety. In addition, the devices provided herein can be readily reused or recycled.

The radiation absorption characteristic of a material is a function of its atomic weight and its density. In addition, radiation attenuation is a function of the thickness of the material. The radiation shielding devices provided herein can be made from any radiation absorbing material including, for example, a thermoplastic or thermosetting material containing a filler (e.g., antimony, titanium dioxide, lead, tungsten, barium sulfate, or a bismuth compound such as the subcarbonate, the trioxide, or the oxychloride). Alternatively, the devices can be made from an absorbing material such as a metal element (e.g., lead or aluminum), compound, alloy (e.g., steel, stainless steel, or brass), blend, and the like. Further, the devices provided herein can be made from a material chosen for improved efficiency. For example, a material can be chosen to match the energy of the radiation source, such that the energy level(s) of atomic particles (e.g., electrons) in the shielding material are comparable to the energy level emitted from the radiation source to be shielded by the device.

The devices can be made using any process that produces shaped articles. Suitable processes include, without limitation, drawing, stamping, forming, molding by injection (e.g., thermoplastic, thermoset, or metal injection molding), compression or transfer molding, machining, milling, or lathing, or a combination of such processes. Radiation shielding devices can have a single piece or can include multiple pieces (e.g., two, three, four, five, or more pieces). For example, a radiation shielding device can include a top piece and a bottom piece, an inner piece and an outer piece, or a combination of such pieces.

Radiation shielding devices can be attached (e.g., reversibly attached) to a seed holding device (e.g., a cartridge or a vial) using any means. In some embodiments, shielding devices can engage a seed cartridge using a means already included in the cartridge. For example, a seed cartridge may include a screw thread. See, e.g., the Mentor-20 cartridge assembly shown in FIG. 1, which defines a screw thread on its outer surface. The radiation shielding devices provided herein can include a surface that defines interior threads adapted to reversibly engage the exterior threads of a seed cartridge such as the Mentor-20 cartridge. Alternatively, shielding devices can engage a seed cartridge or vial using any other suitable means (e.g., mechanical, adhesive, cohesive, or magnetic means). Radiation shielding devices also can be configured to reversibly attach to a seed cartridge by engaging a passive feature of the cartridge (e.g., a collar, groove, slot, undercut, face, or any other feature useful or adaptable for engagement). Thus, the components of a radiation shielding device can engage each other and/or a radiation source by means including, without limitation, a screw fit, a snap fit, or a bayonet fit.

Some seed cartridges have radiation shielding in particular areas relative to the location of the seeds. In such embodiments, a radiation shielding device (e.g., a cap or a cover) can be applied to the unshielded areas using an attachment or fixation means such as those described herein. For cartridges or containers for which shielding in several or all directions is desired, a capsule or enclosure consisting of one part or more than one part (e.g., two or more parts) can be used. Such a device can include, for example, a container and a closure, or a multi-piece housing with parts configured to surround the radioactive source. The device can have features through which the cap, cover, or assembly can be secured (e.g., reversibly secured) to enclose the seed container either entirely or partially. Whether the device includes one part or more than one part, it can be adapted to (a) engage a radiation source (e.g., a loaded seed magazine or a vial containing radioactive seeds) and provide radiation shielding for a user, (b) be removable from the radiation source to allow for seed assay, end use, and the like without hampering normal use, and (c) be redeployed as necessary for further transport or sterilization of the radiation source, for example.

The radiation shielding devices provided herein can have any size and shape. For example, a shielding device can be configured to surround or shield all or a portion of a vial or a cartridge that can contain a plurality of radioactive brachytherapy seeds. Radiation shielding devices can include one or more members with an interior surface and an exterior surface, and the interior surface can be configured to contain or abut a radiation source (e.g., a vial or a seed cartridge, or a compartment of a seed cartridge configured to retain one or more radioactive brachytherapy seeds). The interior surface can define any shape (e.g., an arc, a flat plane, a circle, an oval, a polygon such as a triangle, a square, a rectangle, a pentagon, a hexagon, or an octagon, or a shape adapted to receive a radiation source having a particular shape). The exterior surface also can define any shape (e.g., a circle, an oval, a triangle, a square, a pentagon, a hexagon, or an octagon). In one embodiment, a shielding device can include a hollow cylinder with at least one open end. Such a device can have interior and exterior surfaces that define circles when the device is viewed from the ends. In another embodiment, a shielding device can be hollow and have (a) an interior surface configured to receive all or a portion of a radiation source, (b) an exterior surface that defines an octagon, and (c) one open end configured to receive the radiation source.

The radiation shielding devices provided herein can have any dimensions. For example, a device can be between about 5 mm and 150 mm in length (e.g., between about 10 mm and about 100 mm, between about 25 mm and about 90 mm, or between about 40 mm and about 80 mm in length). A device can be between about 2 mm and about 20 mm in width (e.g., between about 4 mm and about 18 mm, between about 6 mm and about 16 or between about 8 mm and about 14 mm in width).

A device can have an inner diameter between about 3 mm and about 7 mm (e.g., between about 4 mm and about 6 mm, or between about 4.5 mm and about 5.5 mm). In one embodiment, a device can have an inner diameter of about 5 mm. A device can have an outer diameter between about 20 mm and about 40 mm (e.g., between about 25 mm and 35 mm, or between about 27 mm and about 33 mm). In one embodiment, a device can have an outer diameter of about 30 mm.

Furthermore, the devices provided herein can have any thickness. For example, a device can be between about 0.1 mm and about 10 mm in thickness (e.g., between about 0.25 mm and about 5 mm, between about 0.5 mm and about 7.5 mm, or between about 0.8 mm and about 2.5 mm in thickness) between, e.g., its inner and outer surfaces. In some embodiments, a useful thickness for a device can be determined based on the half-value layer of the material from which the device is constructed. The half-value layer is the thickness of a substance that reduces the intensity of a beam of radiation to one-half of its initial value. The half-value layer is a function of the energy of the radiation and the composition of the shield or absorber. The thickness of the thinnest section required for attenuation of a radiation source, given the effectiveness of shielding for the material of construction, can be calculated according to the mathematical formula:

$R=(0.5)^{\wedge}(X)$, where

R=residual transmitted radiation, and $X=D/HVL$, where

D=the thickness of the thinnest section of the shielding device, and

HVL=the thickness of the half value layer for the material of construction and radiation source.

The radiation shielding devices provided herein can be configured to facilitate sterilization. For example, a device can define one or more (e.g., one, two, three, four, five, six, seven, eight, nine, ten, or more) features such as a vent, slot, groove, passage, or window extending from the outer surface of a member to the inner surface of the member. Such features can be configured to allow for the passage of, for example, steam during autoclaving, without permitting a direct line of sight to the interior of the device or to a radiation source (e.g., a seed-containing compartment of a seed holding device, such as a magazine of a seed cartridge) contained within the device. For example, features that are openings (e.g., vents, slots, or windows) can be configured such that when a seed cartridge is partially or fully engaged within a radiation shielding device, there is no direct line of sight from the exterior of the device to seed within the magazine or to the seed magazine itself. In some embodiments, a component of a radiation shielding device can have one or more features extending along a straight path between the outer surface and the inner surface of the component; to provide a line of sight from the exterior to the interior of the component. Openings configured in such a manner can be particularly useful in devices that have inner and outer components configured in such a manner that when the inner component is placed into the outer component, the openings are not aligned and there is no direct line of site from the exterior to the interior of the device. Alternatively, such features can extend along a curved or angled path between the outer surface and the inner surface, such that there is no direct line of sight from the exterior to the interior of the device. In other embodiments, a feature such as a groove can be entirely internal to a shielding device. Such features can facilitate venting between, for example, components of a shielding device.

The positioning of features such as those described herein can be fixed (e.g., reversibly fixed) with respect to the seed cartridge or vial contained within the device. In some embodiments, a shielding device can be constructed of two or more pieces that each define one or more features such as those described herein. The two or more pieces can be adapted to be fixed (e.g., reversibly fixed) relative to each other and to the radiation source, such that any emitted radiation is substantially or completely occluded.

The invention is further described in the examples that are shown in FIGS. 1-15 and described in the following paragraphs. These embodiments do not limit the scope of the invention described in the claims.

Figure 2:
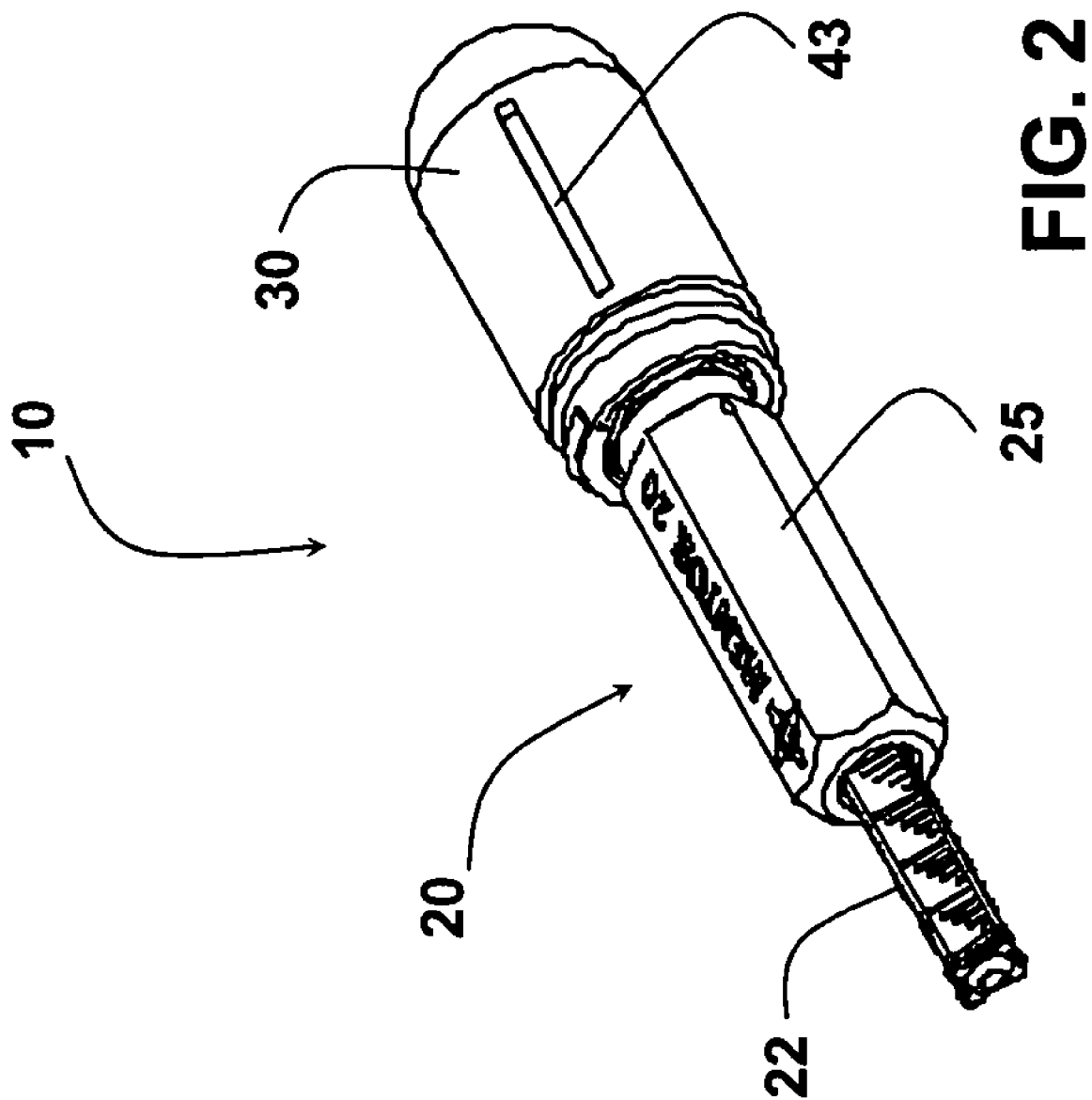
FIG. 2 is a diagram of the radiation shielding device of FIG. 1 engaged with a seed cartridge.

With reference to FIGS. 1 and 2, radiation shielding device 10 can be configured to engage seed cartridge 20. Seed cartridge 20 can include stem 22, housing 25, and magazine 27, which typically is configured to retain a plurality (e.g., between 1 and 20) of brachytherapy seeds. Thus, radiation may be emitted from magazine 27 when seed cartridge 20 contains one or more seeds. In some embodiments, a radiation shielding device (e.g., device 10) can be configured to provide shielding for the portion of cartridge 20 that includes magazine 27, as shown in FIG. 2.

Shielding device 10 can include outer member 30 and inner member 32. Outer member 30 can be hollow and can have open end 34 and inner surface 35, such that outer member 30 is adapted to receive inner member 32. Inner member 32 can be hollow and can have open end 36 and inner surface 37, such that inner member 32 is adapted to receive seed cartridge 20. In some embodiments, inner member 32 can be adapted to receive magazine 27 in particular. In addition, outer member 30 and inner member 32 can have distal ends 38 and 39 opposite open ends 34 and 36, respectively.

Outer member 30 and inner member 32 can define one or more openings to facilitate sterilization, for example. As shown in FIGS. 1 and 2, outer member 30 can define vents 43 and 44, and inner member 32 can define vents 46 and 47. In addition, outer member 30 and inner member 32 can define mating features such as grooves 55 and 56 (not visible), and fins 58 and 59. Fins 58 and 59 can be configured to slidably engage grooves 55 and 56, respectively. In such an embodiment, inner member 32 can be inserted into open end 34 of outer member 30 such that inner member 32 can be reversibly retained in a fixed position within outer member 30. Thus, device 10 can be configured such that when inner member 32 and outer member 30 are engaged with each other, they are aligned such that there is no direct line of sight from the exterior of outer member 30 to the interior of inner member 32, other than at open ends 34 and 36. In addition, distal ends 38 and 39 can be open or closed. Typically, at least one of distal ends 38 and 39 is closed, so as to prevent a direct line of sight from the exterior of outer member 30 to a radiation source (e.g., a magazine containing one or more seeds) within device 10. Alternatively, distal ends 38 and 39 both can be partially open, such that when inner member 32 is placed within outer member 30, the openings in distal ends 38 and 39 are not aligned and there is no direct line of sight into the interior of device 10.

In addition, open end 34 of outer member 30 can define internal thread 60, which can be adapted to engage external thread 63 of housing 25. Thus, inner member 32 can be inserted into outer member 30, and the shielding assembly can be screwed onto seed cartridge 20 to surround and provide radiation shielding for magazine 27. FIG. 2 shows the assembly of seed cartridge 20 with radiation shielding device 10. As shown in FIGS. 1 and 2, stem 22 and housing 25 may not be shielded by device 10. Again, due to the manner in which outer member 30 and inner member 32 are connected, and the arrangement of vents 43, 44, 46, and 47, there may be no direct line of sight from the exterior of device 10 to a radiation source (e.g., a magazine containing one or more seeds) within device 10.

Figure 3:
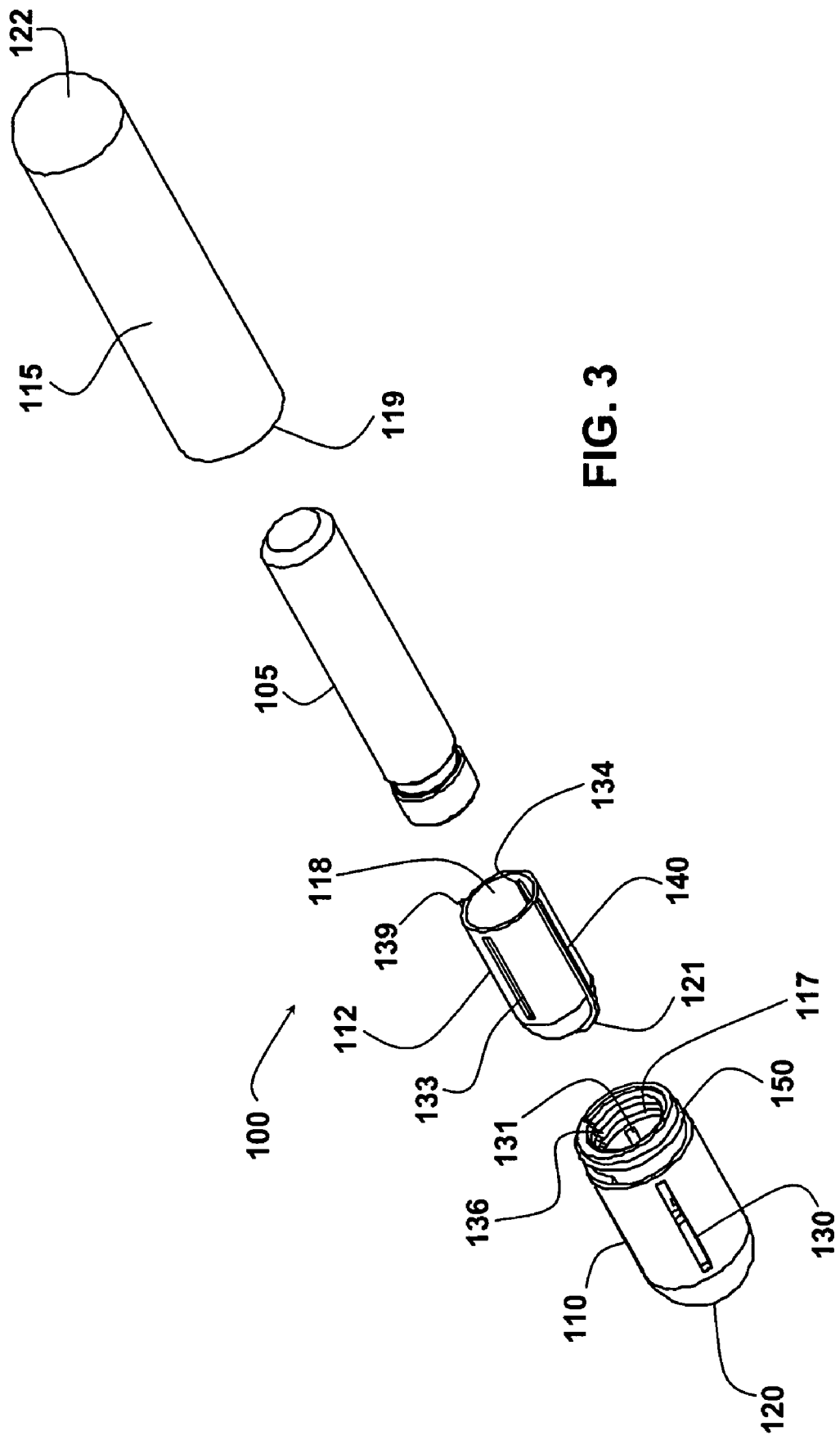
FIG. 3 is a diagram of a vial and a three-part radiation shielding device.
Figure 4:
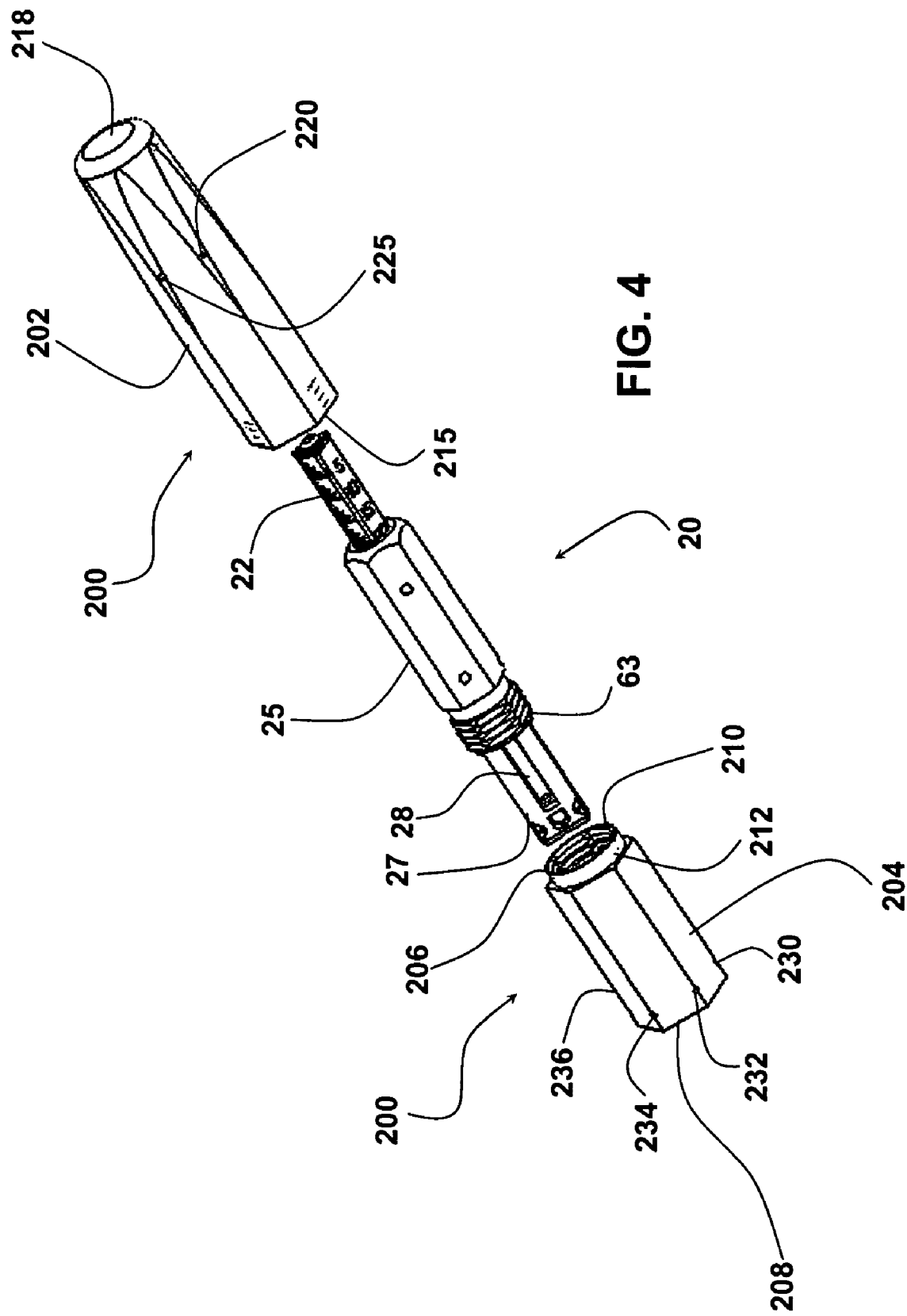
FIG. 4 is a diagram of a seed cartridge and a radiation shielding device having a top piece and a bottom piece.

An alternative embodiment is illustrated in FIG. 3. Radiation shielding device 100 can be adapted to provide shielding for a radiation source in vial 105. Radiation shielding device 100 can be configured to completely surround and shield vial 105. As shown in FIG. 3, device 100 can include bottom outer member 110, bottom inner member 112, and top member 115. Bottom outer member 110 can be hollow and can have open end 117, such that bottom outer member 110 is adapted to receive bottom inner member 112. Bottom inner member 112 can be hollow and can have open end 118, such that bottom inner member 112 is adapted to receive at least a portion of vial 105. Similarly, top member 115 can be hollow and can have open end 119, such that top member 115 is adapted to receive at least a portion of vial 105. In addition, bottom outer member 110, bottom inner member 112, and top member 115 can have distal ends 120, 121, and 122 opposite open ends 117, 118, and 119, respectively. Distal ends 120, 121, and 122 can be open or closed. Typically, at least one of distal ends 120 and 121 is closed, so as to prevent a direct line of sight from the exterior of bottom outer member 110 to a radiation source (e.g., a magazine containing one or more seeds) within device 100. Alternatively, distal ends 120 and 121 both can be partially open, such that when bottom inner member 112 is placed within bottom outer member 110, the openings in distal ends 120 and 121 are not aligned and there is no direct line of sight into the interior of device 100.

Bottom outer member 110 and bottom inner member 112 also can define one or more openings. For example, bottom outer member 110 can define vents 130 and 131, and bottom inner member 112 can define vents 133 and 134. In addition, bottom outer member 110 and bottom inner member 112 can define one or more mating features. For example, bottom outer member 110 can define grooves 136 and 137 (not visible in FIG. 3), and bottom inner member 112 can define fins 139 and 140. In use, bottom inner member 112 can be inserted into bottom outer member 110 such that fins 139 and 140 slidably engage grooves 136 and 137, respectively. Vents 130, 131, 133, and 134 can be positioned such that when top inner member is engaged within bottom outer member 110, there is no direct line of sight from the exterior of bottom outer member 110 to the interior of bottom inner member 112.

Bottom outer member 110 and/or bottom inner member 112 can be configured to engage top member 115 using any means. For example, top outer member 115 can define external thread 150, which can be adapted to engage an internal thread (not visible) defined by top member 115. Alternatively, the top assembly of device 100 can engage top member 115 using any other means (e.g., a snap fit, a spring fit, or a bayonet joint). Thus, vial 105 can be reversibly and completely contained within device 100 such that any radiation source within vial 105 is effectively shielded.

FIGS. 4-7 show another embodiment of a radiation shielding device. With respect to FIGS. 4-7, device 200 can include top member 202 and bottom member 204, which can be adapted to engage each other and/or seed cartridge 20. In this embodiment, bottom member 204 can be configured to surround and shield magazine 27, while top member 202 can be configured to surround and shield stem 22 and housing 25.

Bottom member 204 can be hollow and can have open end 206, such that bottom member 204 is adapted to receive magazine 27. In addition, bottom member 204 can have distal end 208 opposite open end 206. Distal end 208 can be open or closed. The interior surface of open end 206 can define thread 210, which can be adapted to engage external thread 63 of housing 25. In addition, the exterior surface of open end 206 can define thread 212.

Figure 7:
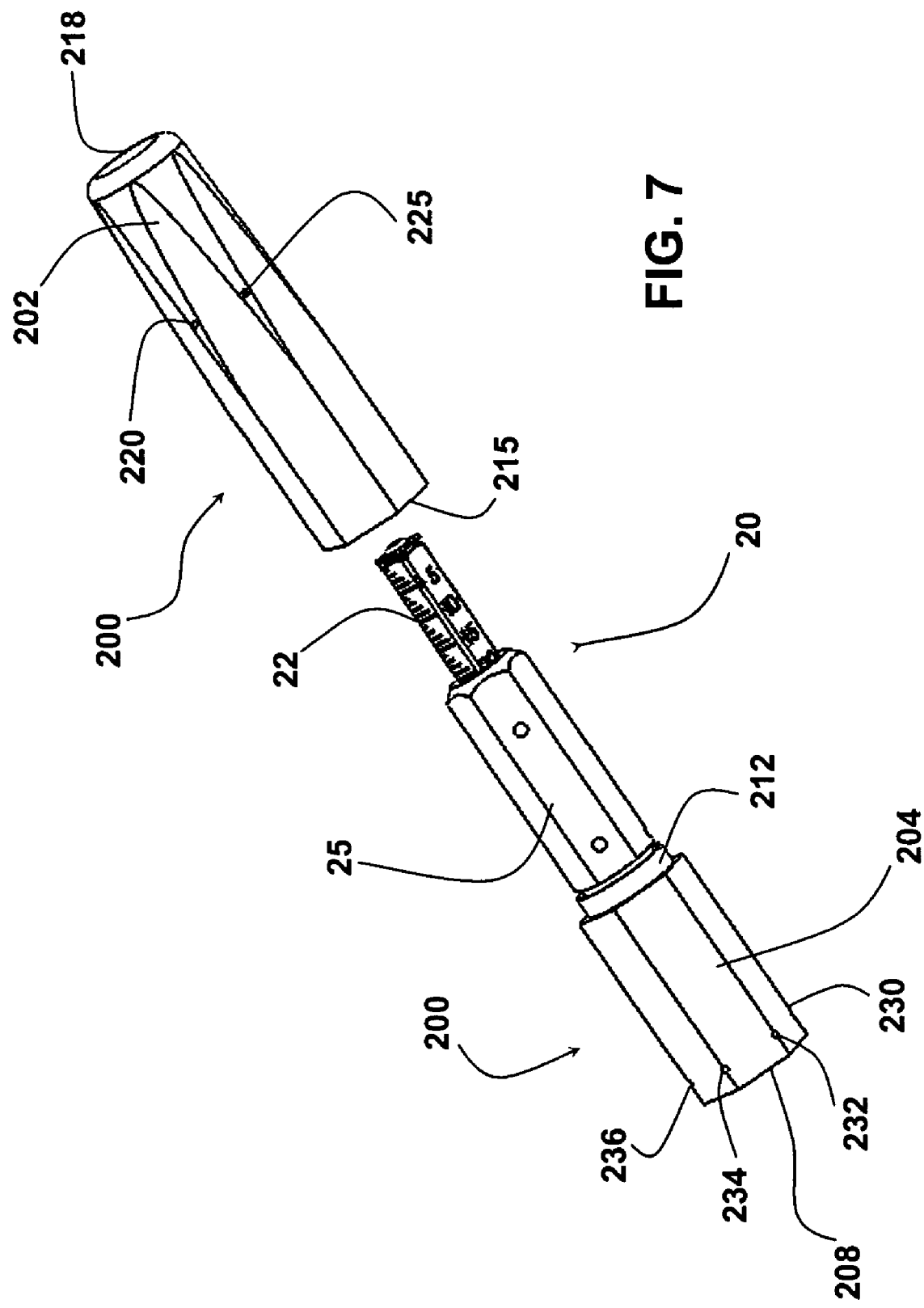
FIG. 7 is a diagram of the radiation shielding device of FIG. 4, showing the bottom piece engaged with a seed cartridge.
Figure 8:
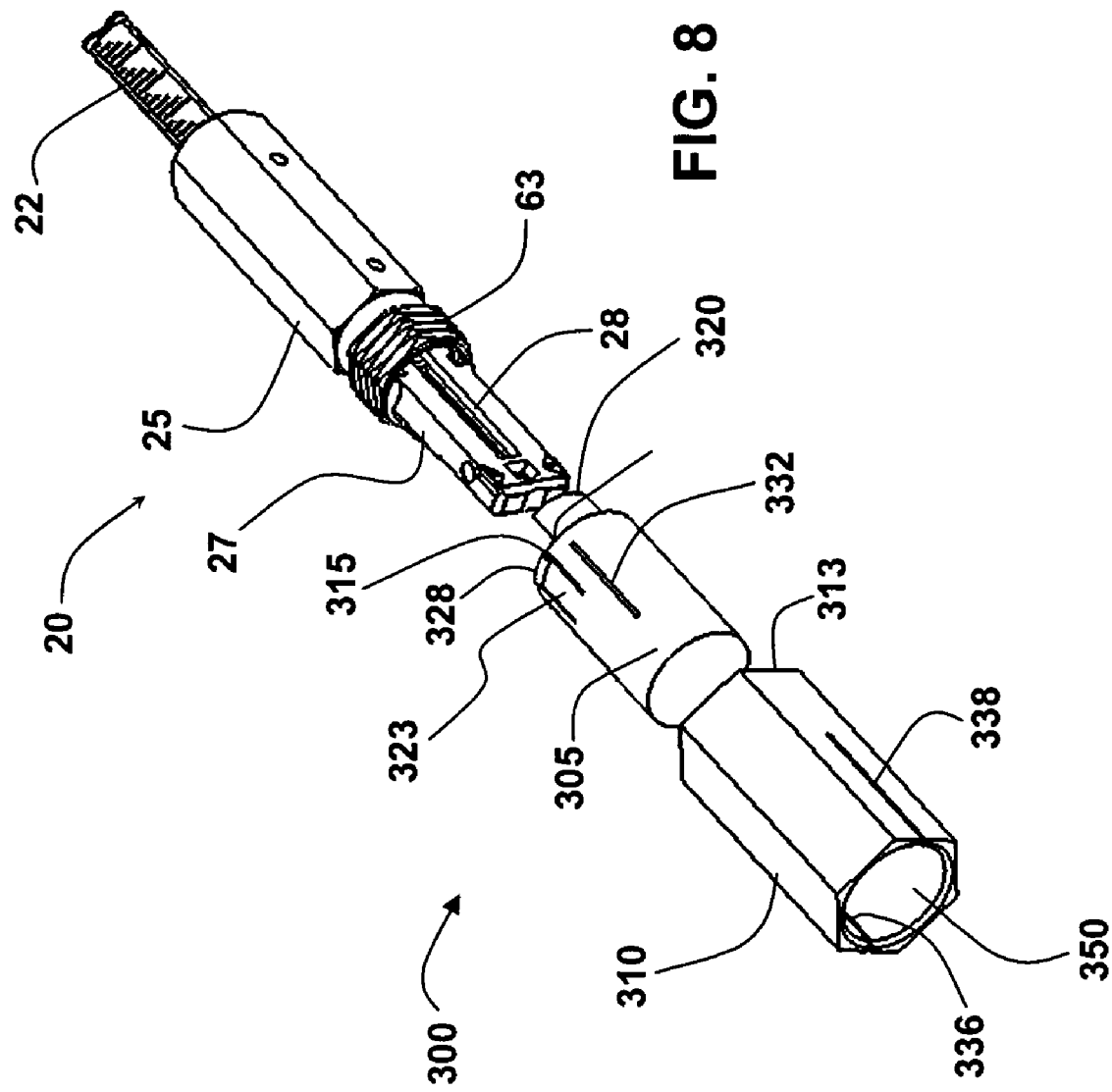
FIG. 8 is a diagram of a seed cartridge and a radiation shielding device having an inner piece and an outer piece.

Top member 202 also can be hollow, and can have open end 215 such that top member 202 is adapted to receive stem 22 and housing 25. Top member 202 also can have distal end 218 opposite open end 215. Distal end 218 can be open or closed. In addition, the internal surface of open end 215 can define screw thread 217, which can be adapted to engage external thread 212 defined by bottom member 204. Thus, bottom member 204 can be screwed onto seed cartridge 20 as shown in FIG. 7, for example, and top member 202 can be screwed onto the bottom member/seed cartridge assembly. Alternatively, any other method can be used for engagement of the components of device 200 with each other and with seed cartridge 20, as described herein.

Figure 5:
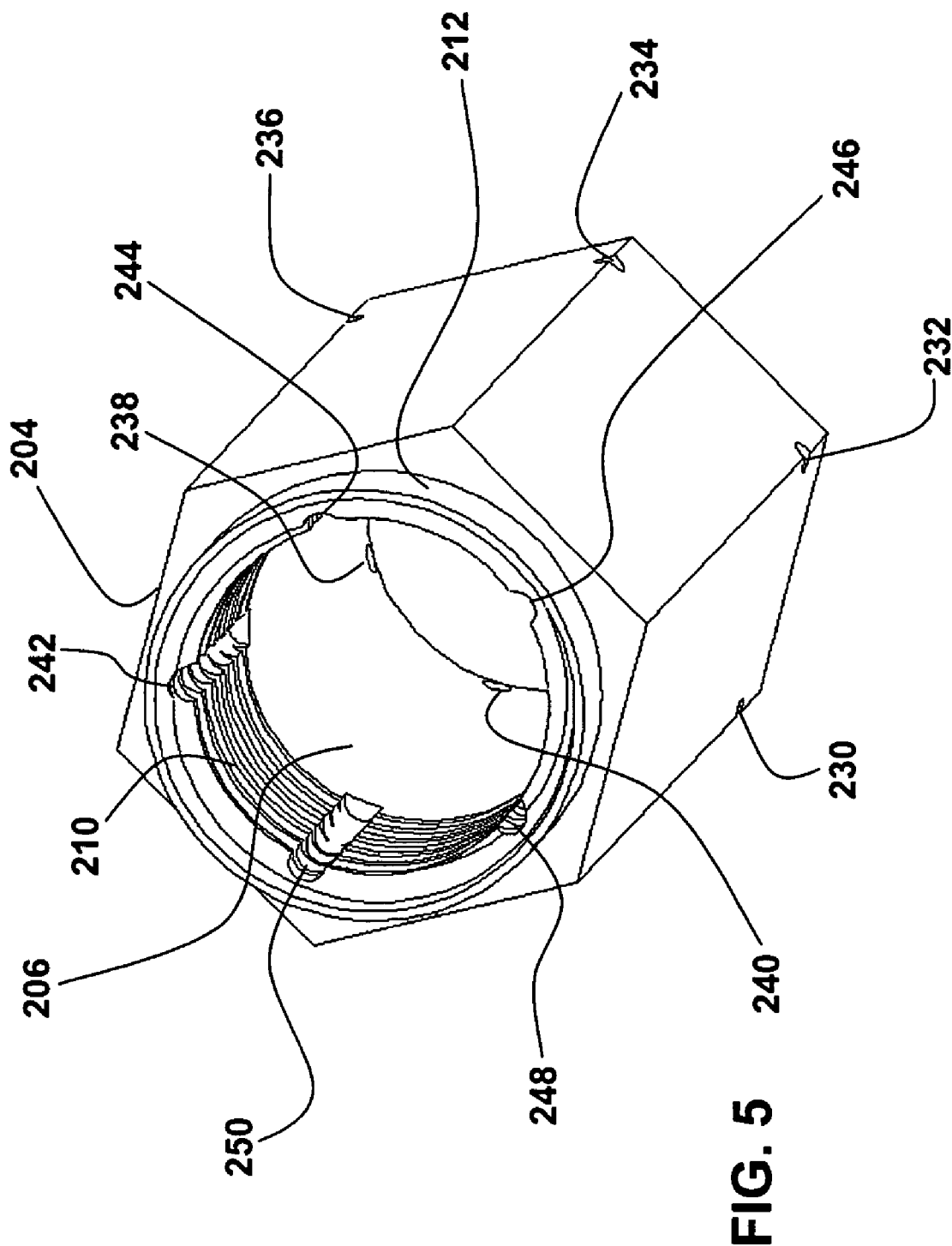
FIG. 5 is a close-up, overhead perspective view of the bottom piece of the radiation shielding device of FIG. 4.
Figure 6:
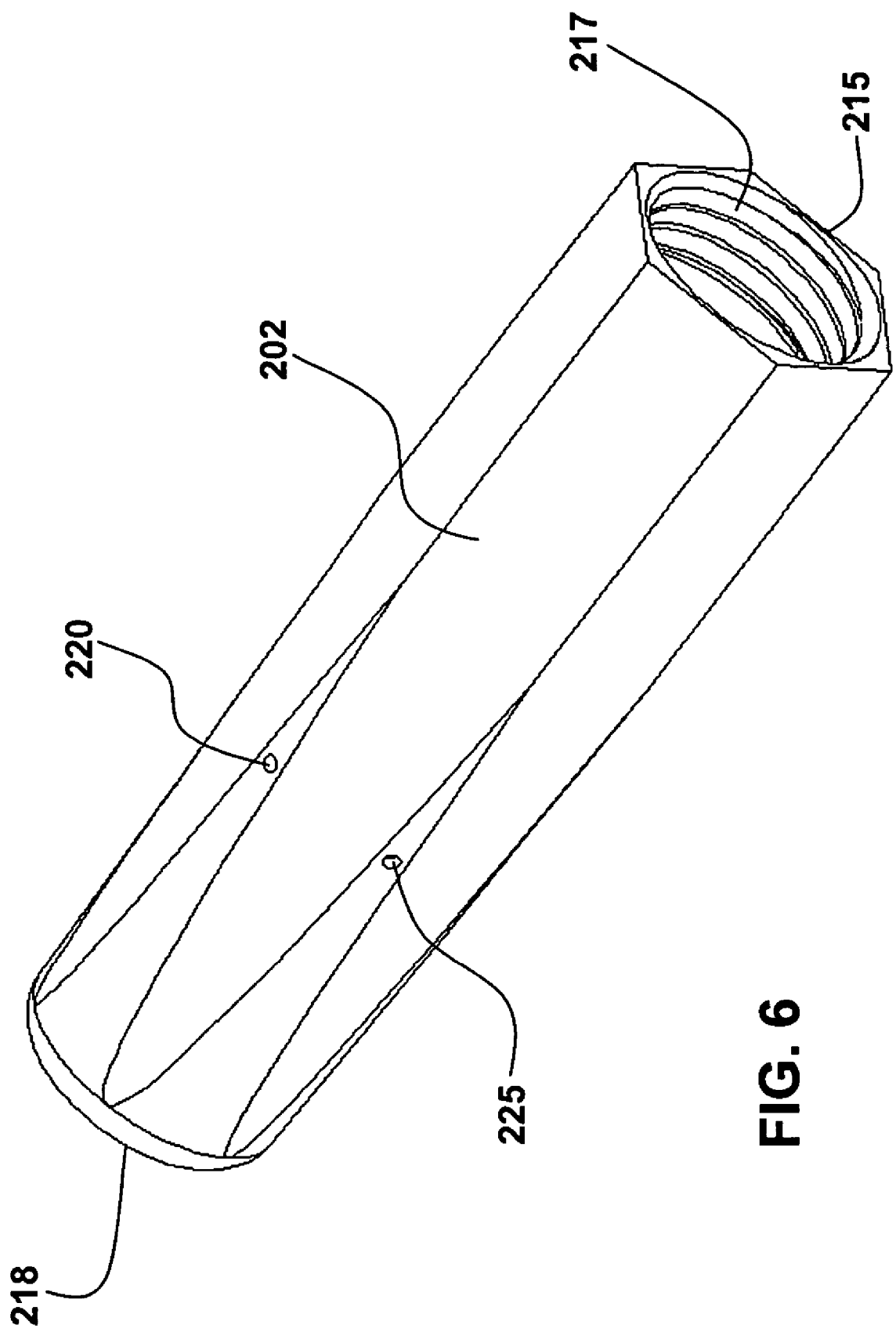
FIG. 6 is a close-up view of the top piece of the radiation shielding device of FIG. 4.

As shown in FIGS. 4-7, top member 202 and bottom member 204 can define one or more openings to, for example, facilitate sterilization. For example, top member 202 can define vents 220 and 225, and bottom member 204 can define vents 230, 232, 234, 236, 238, and 240. Such openings can be positioned such that there is no direct line of sight from the exterior of device 200 to a radiation source (e.g., a magazine containing one or more seeds) contained therein. For example, vents 230, 232, 234, 236, 238, and 240 can be positioned such that when a seed cartridge is contained within device 200, they do not provide a direct line of sight to any openings (e.g., seed window 28) in magazine 27 through which radiation can directly escape. Further, the openings in top member 202 and bottom member 204 can be positioned in areas that are the thickest with respect to the distance between the exterior surface and the interior surface. As shown in FIG. 5, for example, vents 230, 232, 234, 236, 238, and 240 can be positioned at the thickest points of bottom member 204. Similarly, vents 220 and 225 can be positioned near the thickest points of top member 202, as shown in FIG. 6. Positioning at the thickest points may be more critical for openings defined by bottom member 204, which is adapted to provide shielding for magazine 27.

Vents 220, 225, 230, 232, 234, 236, 238, and 240 can extend between the outer surface and the inner surface of top member 202 and bottom member 204. Device 200 also can define one or more notches adapted to provide venting between top member 202 and bottom member 204. As shown in FIG. 5, for example, bottom member 204 can define notches 242, 244, 246, 248, and 250 in thread 210. When bottom member 204 is screwed onto seed cartridge 20 at external thread 63, which as shown can define a hexagonal shape, at least one of notches 242, 244, 246, 248, and 250 can provide venting between bottom member 204 and top member 202.

While device 200 can provide shielding for an entire seed cartridge, the radiation shielding device shown in FIGS. 8-12 can be adapted to provide shielding to a portion of a radiation source such as seed cartridge 20. For example, device 300 can be configured to provide shielding to magazine 27 of cartridge 20, while not providing shielding to stem 22 or housing 25. Device 300 can include inner member 305 and outer member 310, which are shown in greater detail in FIGS. 9 and 10, respectively. Inner member 305 and outer member 310 can be hollow, and can have at least one open end. For example, outer member 310 can have open end 313, and can be adapted to receive inner member 305. Similarly, inner member 305 can have open end 315, and can be adapted to receive magazine 27. In some embodiments, both ends of outer member 310 and inner member 305 can be open.

Inner member 305 and outer member 310 can be adapted to engage each other and at least a portion (e.g., magazine 27 and/or screw thread 63 on housing 25) of seed cartridge 20. For example, the interior surface of outer member 310 can define internal thread 318, which can be adapted to engage external thread 63 of housing 25. Further, the interior of inner member 305 can be shaped to mate with the exterior surface of magazine 27 and to provide maximal shielding for radiation emitted by seeds contained within magazine 27. When magazine 27 is rectangular, for example, the interior of inner member 305 can define a rectangular well with dimensions just slightly larger (e.g., 0.1 mm to 0.25 mm larger in length and width) than the dimensions of magazine 27.

Further, inner member 305 can be configured such that maximal shielding is provided to the face of magazine 27 that defines seed window 28. For example, inner member 305 can have extension 320 (shown in FIGS. 8 and 9), which can extend into housing 25 and shield window 28 when device 300 is assembled and engaged with seed cartridge 20.

Figure 9:
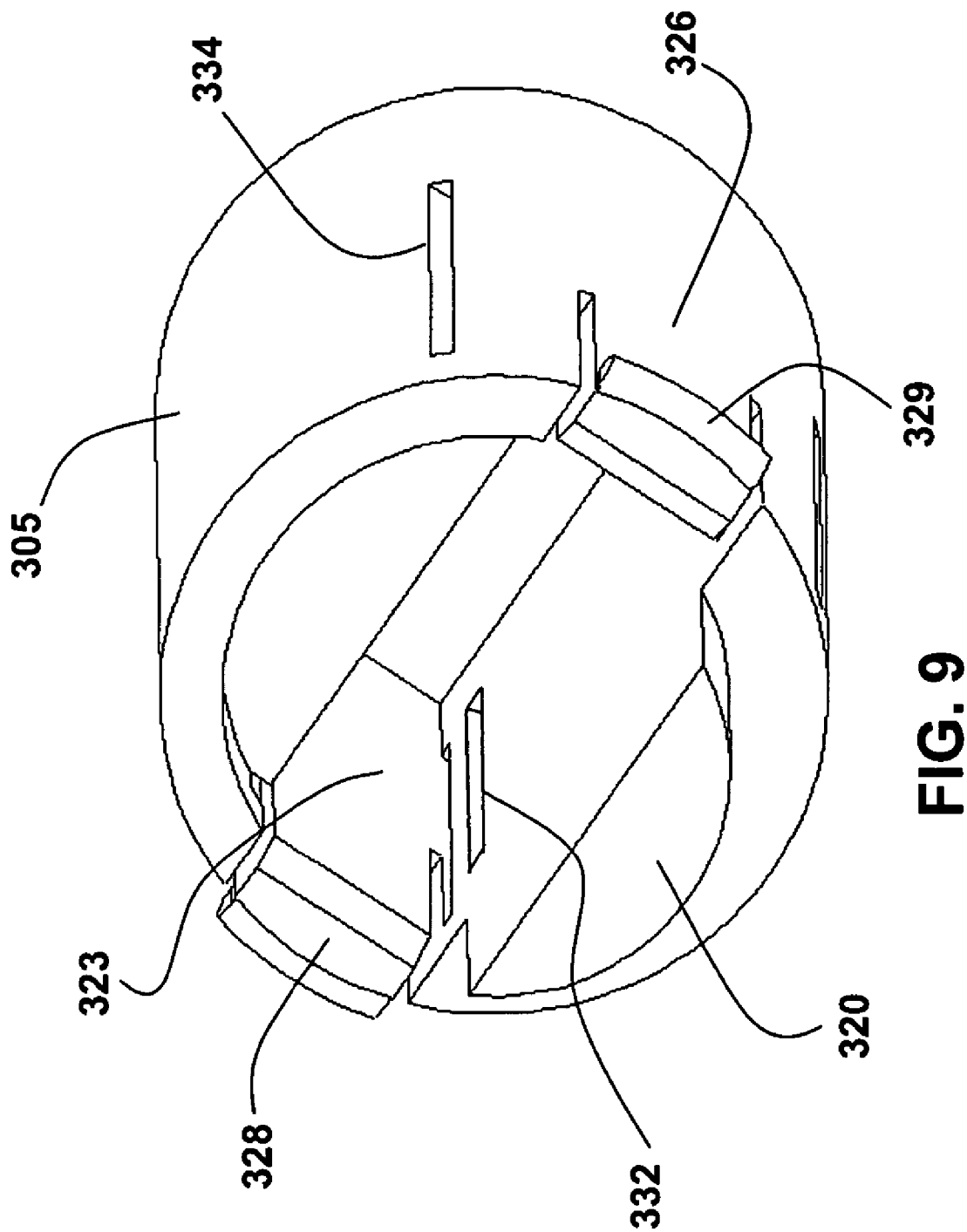
FIG. 9 is a close-up view of the inner piece of the radiation shielding device of FIG. 8.
Figure 10:
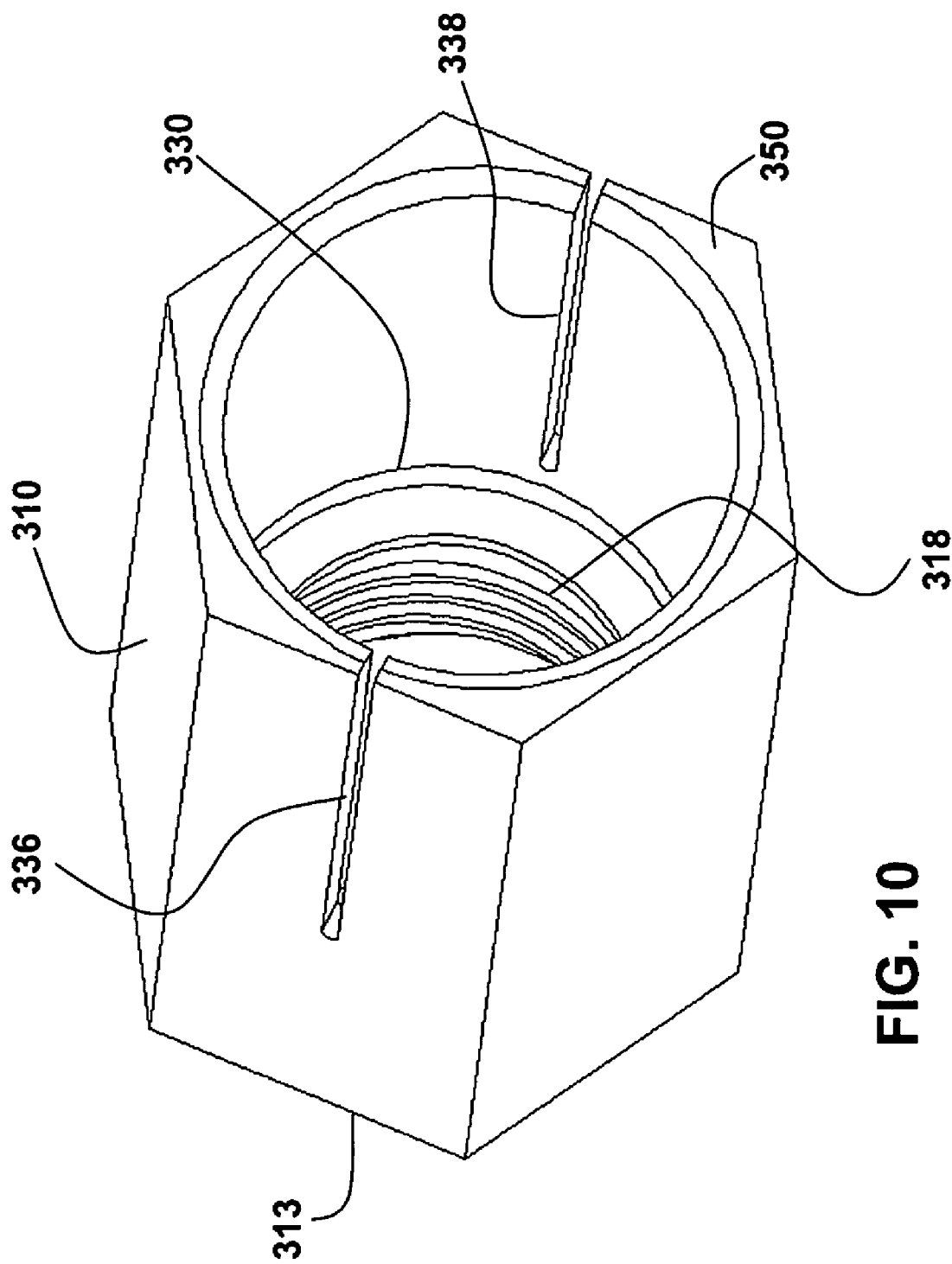
FIG. 10 is a close-up view of the outer piece of the radiation shielding device of FIG. 8.
Figure 11:
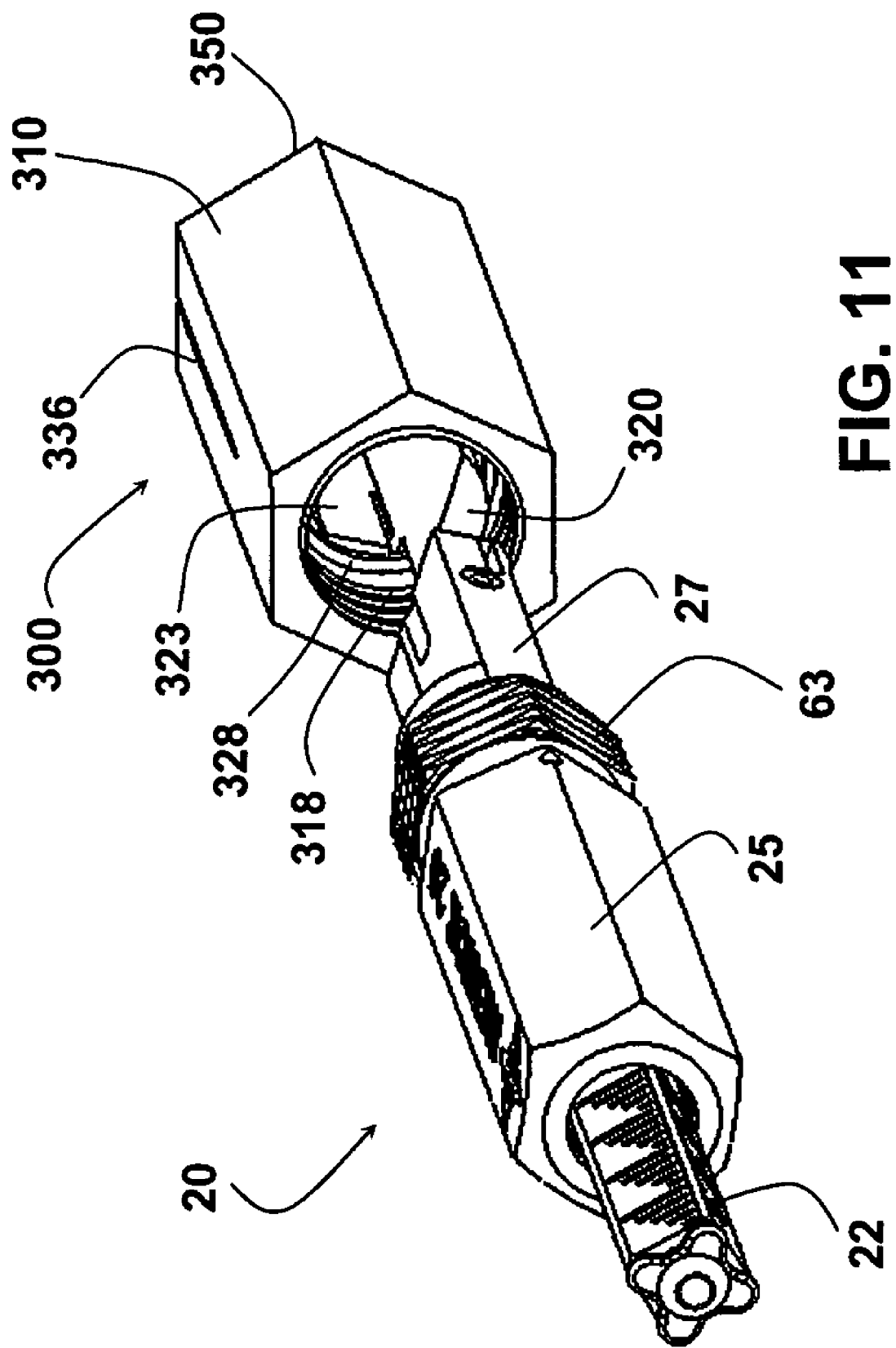
FIG. 11 is a diagram of a seed cartridge and the assembled radiation shielding device of FIG. 8.
Figure 12:
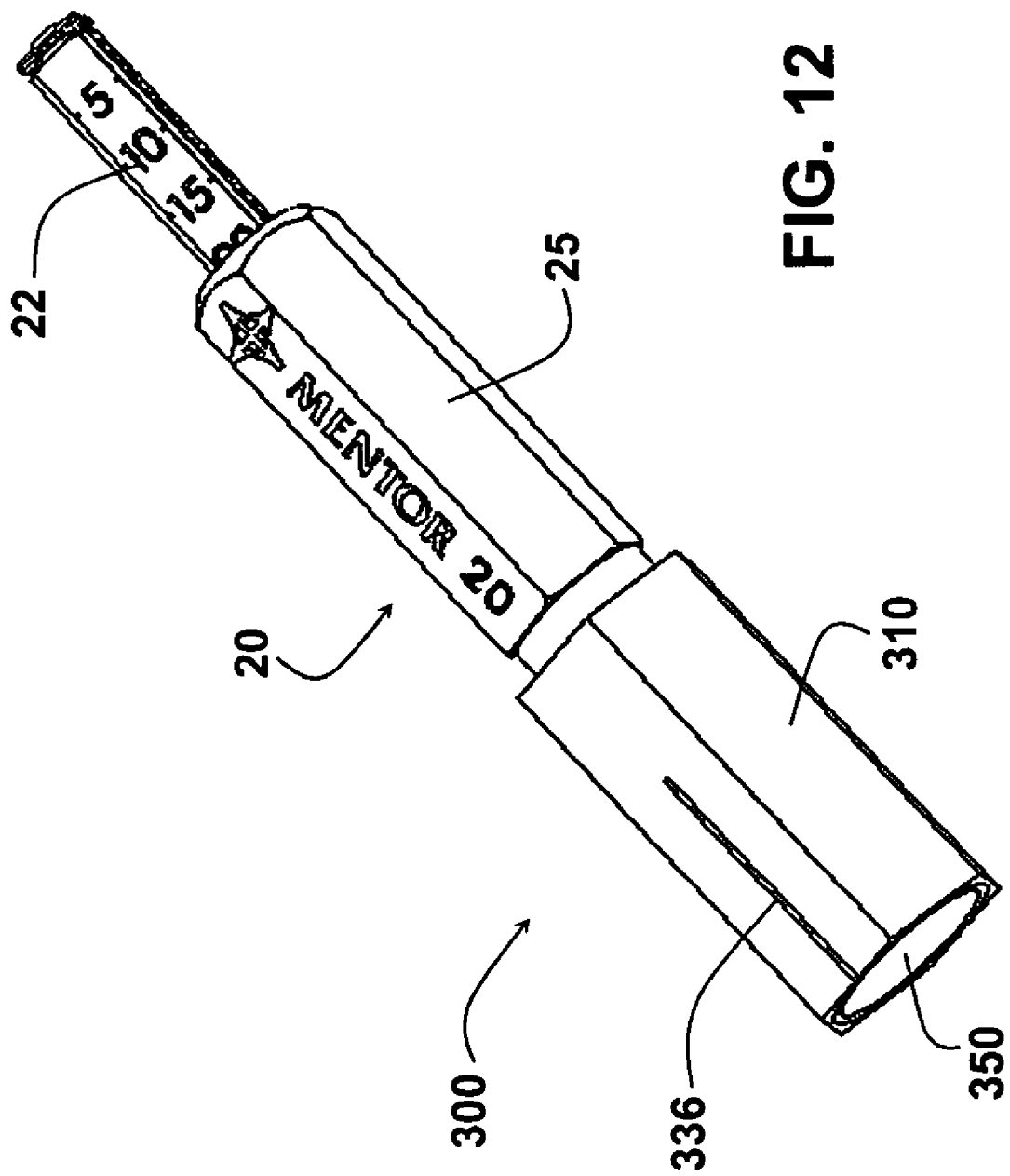
FIG. 12 is a diagram of the radiation shielding device of FIG. 8 as it appears when engaged with a seed cartridge.
Figure 13:
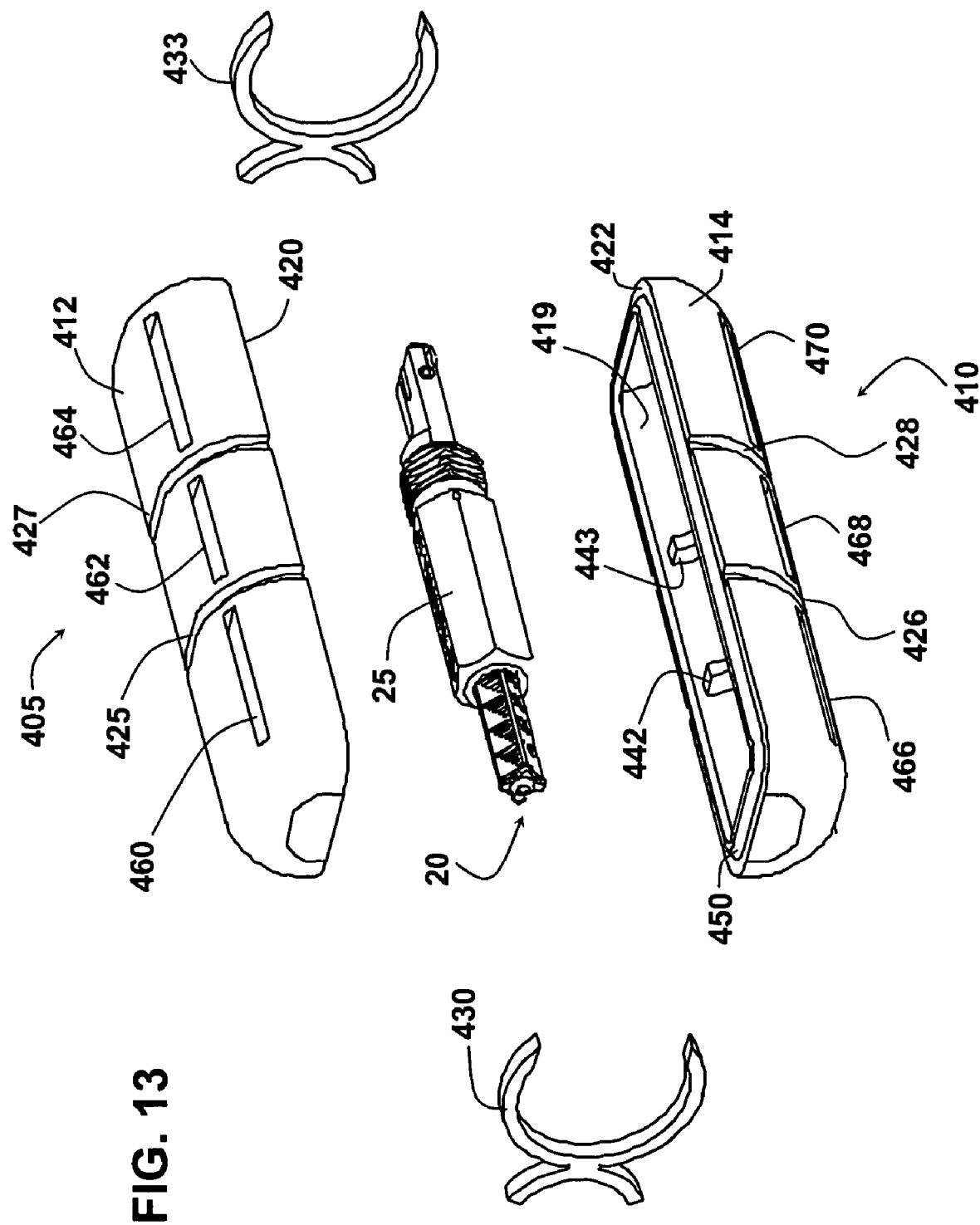
FIG. 13 is a diagram of a seed cartridge and a radiation shielding device having a first piece and a second piece.

With further reference to FIGS. 9 and 10, inner member 305 and outer member 310 can be adapted to reversibly engage one another. For example, inner member 305 can include cantilever springs 323 and 326, which can define protrusions 328 and 329, respectively. Protrusions 328 and 329 can extend radially away from inner member 305. The interior surface of outer member 310 can define groove 330, such that when inner member 305 is inserted into outer member 310, protrusions 328 and 329 can engage groove 330 and retain inner member 305 in outer member 310. As shown in Figure 10, groove 330 can extend completely around the interior surface of outer member 310. In this embodiment, inner member 305 can rotate with respect to outer member 310 when protrusions 328 and 329 are engaged in groove 330. In another embodiment, the outer member of a shielding device can define a groove or a notch for each corresponding cantilever spring extension of the inner member. Each such groove can be long enough to allow for partial rotation of the inner member within the outer member, or may be long enough only to engage the cantilever spring protrusions while allowing essentially no rotation. To use device 300, inner member 305 can be inserted into outer member 310 such that protrusions 328 and 329 engage groove 330, magazine 27 of seed cartridge 20 can be inserted into open end 315, and the shielding assembly can be screwed onto housing 25 as illustrated in FIG. 12. In some embodiments, inner member 305 can be adapted such that cantilever springs 323 and 326 are held within groove 330 by magazine 27. In either case, device 300 can be configured such that inner member 305 is not separable from outer member 310 unless device 300 is removed from seed cartridge 20.

With additional reference to FIGS. 9 and 10, inner member 305 can define vents 332 and 334 to facilitate sterilization, for example. Similarly, outer member 310 can define vents 336 and 338. Vents 332, 334, 336, and 338 can be positioned such that when inner member 305 is inserted into outer member 310, there is no direct line of sight from the exterior to the interior of device 300. For example, vents 332 and 334 can be positioned toward open end 315 of inner member 305, while vents 336 and 338 can be positioned toward distal end 350 of outer member 310. In such a configuration, there is no direct line of sight from the exterior to the interior of device 300 through vents 336 and 338, even when outer member 310 and inner member 305 are engaged and are rotated relative to one another.

FIGS. 13-16 depict another embodiment of a shielding device as provided herein. Device 400 can have first member 405 and second member 410, which can be configured to engage one another and completely shield seed cartridge 20. First and second members 405 and 410 can have exterior surfaces 412 and 414, interior surfaces 417 and 419, and mating edges 420 and 422.

Exterior surfaces 412 and 414 can define indentations adapted to receive a means by which to hold first and second members 405 and 410 together. For example, exterior surfaces 412 and 414 can define recesses 425, 426, 427, and 428. Recesses 425-428 can be configured such that when mating edges 420 and 422 are placed against one another, recesses 425 and 426 form a contiguous channel adapted to receive a connector such as clip 430, while recesses 427 and 428 form a contiguous channel adapted to receive a connector such as clip 433. Clips 430 and 433 can be made from a flexible material (e.g., plastic or metal), such that when they are placed around device 400 in the channels formed by recesses 425-428, they exert force against exterior surfaces 412 and 414 to hold first and second members 405 and 410 together.

Interior surfaces 417 and 419 can define one or more protrusions. For example, interior surface 419 can define ridges 440 and 442. When device 400 contains seed cartridge 20, ridges 440, 441 (shown in FIG. 14B), 442, and 443 (shown in FIG. 13) can hold seed cartridge 20 away from interior surfaces 417 and 419. Such a configuration can facilitate steam access to seed cartridge 20 during autoclaving, for example. In some embodiments, ridges 440 and 442 can be adapted to mate with a portion of seed cartridge 20, such that seed cartridge 20 is prevented from freely moving when it is contained within device 400. For example, ridges 440 and 442 can be positioned just beyond the ends of housing 25, and can prevent seed cartridge 20 from moving longitudinally within device 400.

Figure 14A:
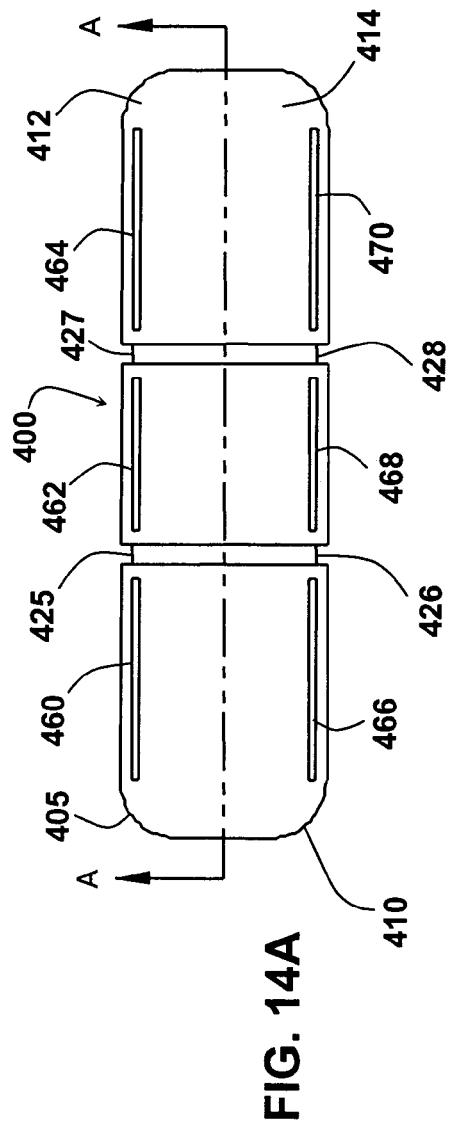
FIG. 14A is a side view of the device of FIG. 13, showing the first and second pieces engaged with each other.

Mating edge 422 of second member 410 can define protrusion 450. Mating edge 420 of first member 405 can define groove 455 (shown in FIG. 15) configured to receive protrusion 450, such that first and second members 405 and 410 can fit snugly together as shown in FIG. 14A, for example. When seed cartridge 20 is contained within device 400, the engagement of protrusion 450 in groove 455 can prevent radiation from escaping between mating edges 420 and 422. Alternatively, mating edge 420 of first member 405 can define a lip configured to extend over a portion of exterior surface 414 of second member 410, thus preventing radiation from escaping between mating edges 420 and 422.

Figure 14B:
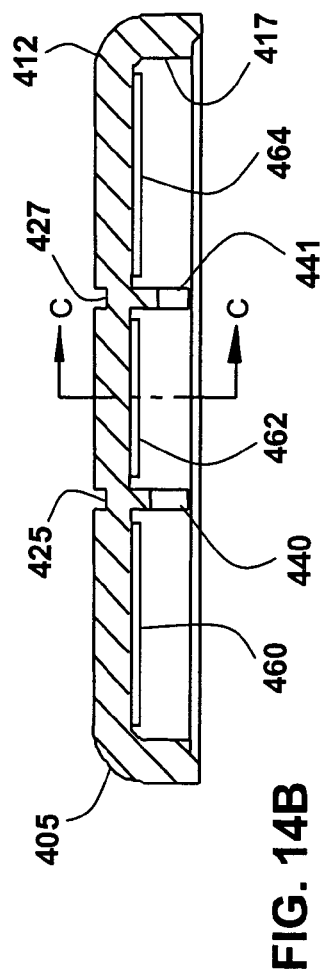
FIG. 14B is a longitudinal cross-sectional view of the first piece, taken along axis A of FIG. 14A.
Figure 14C:
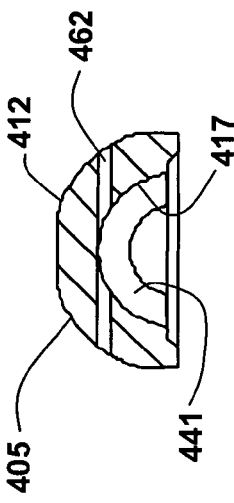
FIG. 14C is a lateral cross-sectional view of the first piece, taken along axis C of FIG. 14B.

First member 405 can define one or more openings extending between exterior surface 412 and interior surface 417. For example, first member 405 can define vents 460, 462, and 464. Similarly, second member 410 can define vents 466, 468, and 470. The openings in first and second members 405 and 410 can be configured such that there is no direct line of sight through the vents from the exterior of device 400 to the interior of device 400. For example, vents 460, 462, 464, 466, 468, and 470 can be curved or angled. Alternatively, vents 460, 462, 464, 466, 468, and 470 can be positioned as shown in FIGS. 14B and 14C, such that there is no direct line of sight to a seed cartridge positioned on ridges 440 and 442 of device 400.

Figure 16:
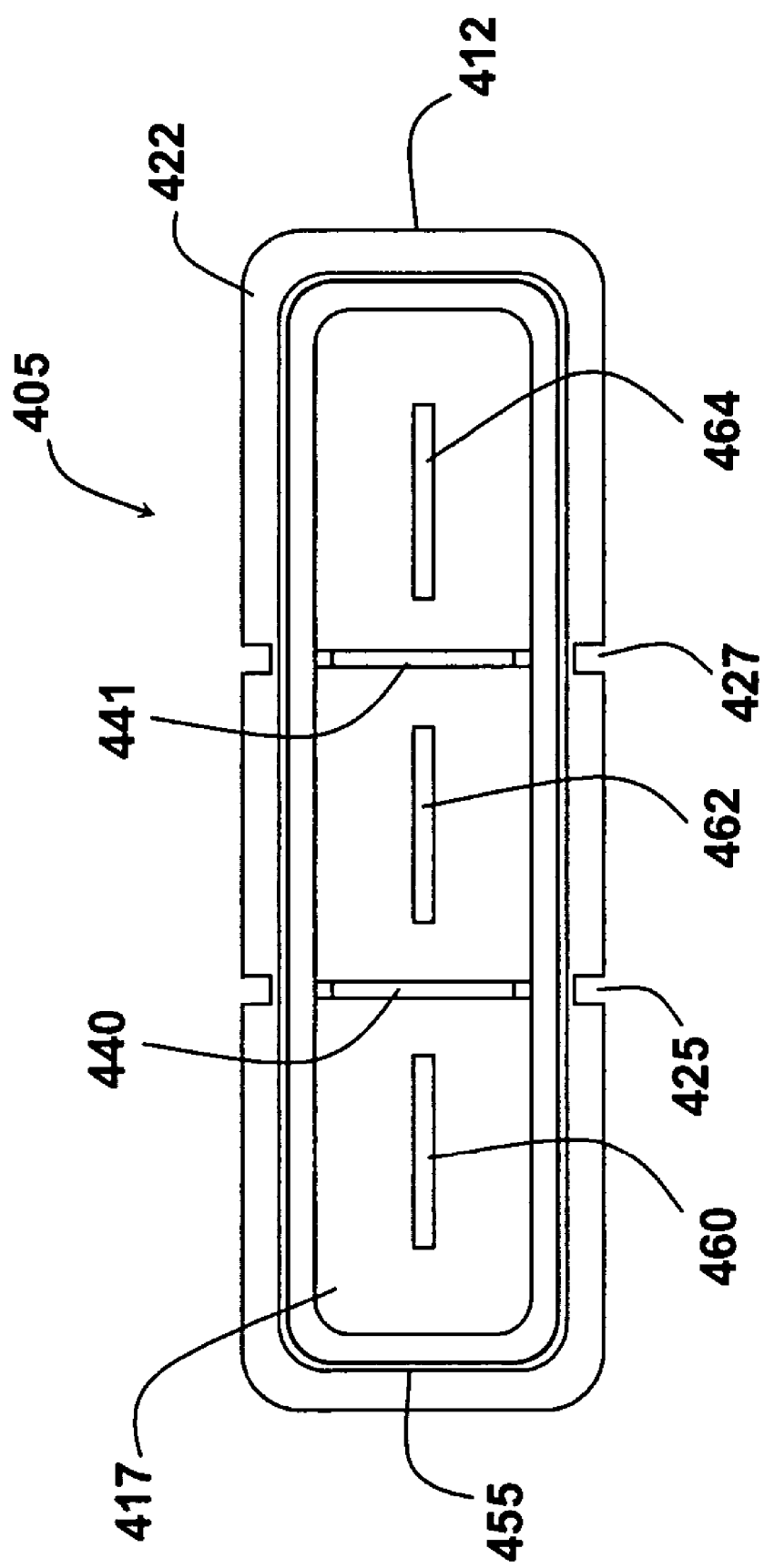
FIG. 16 is a diagram showing an overhead view of the second embodiment of the first piece as shown in FIG. 15.

An alternative embodiment is shown in FIGS. 15 and 16. In the cross-sectional views depicted in FIGS. 15A and 15B, for example, vents 460, 462, and 464 can extend laterally from exterior surface 412 to the interior of first member 405, and can extend vertically from the interior of first side member 412 to interior surface 417. FIG. 16 is an overhead view of first member 405 as depicted in FIG. 15, showing vents 466, 468, and 470 as they extend vertically to interior surface 419.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A brachytherapy seed holding device and a radiation shielding device configured to engage said seed holding device, wherein: a) said seed holding device comprises a radioactive seed contained within a compartment of said seed holding device; b) said radiation shielding device comprises an inner member and an outer member each having an interior surface and an exterior surface; c) said inner member defines an extension configured to shield a window in said compartment and extends over at least a portion of said compartment when said shielding device is engaged with said seed holding device; and d) said inner member defines an opening extending between said interior surface and said exterior surface such that there is no direct line of sight from the exterior of said inner member through said opening to said compartment when said shielding device is engaged with said seed holding device.

2. The seed holding device and shielding device of claim 1, wherein said shielding device is between 25 mm and 90 mm in length.

3. The seed holding device and shielding device of claim 1, wherein said shielding device is between 6 mm and 16 mm in width.

4. The seed holding device and shielding device of claim 1, wherein said shielding device has an inner diameter between 4 mm and 6 mm.

5. The seed holding device and shielding device of claim 4, wherein said inner diameter is about 5 mm.

6. The seed holding device and shielding device of claim 1, wherein said shielding device has an outer diameter between 25 mm and 35 mm.

7. The seed holding device and shielding device of claim 6, wherein said outer diameter is about 30 mm.

8. The seed holding device and shielding device of claim 1, wherein said seed holding device defines an external screw thread, wherein said interior surface of said member defines an internal screw thread, and wherein said internal screw thread is configured to engage said external screw thread.

9. The seed holding device and shielding device of claim 1, wherein there is no direct line of sight from the exterior of said member through said opening to said compartment when said shielding device is fully engaged with said seed holding device.

10. The seed holding device and shielding device of claim 1, wherein there is no direct line of sight from the exterior of said member through said opening to said compartment when said shielding device is partially engaged with said seed holding device.

11. The seed holding device and shielding device of claim 1, wherein said inner and outer members are adapted to engage one another through a snap fit, a bayonet fit, or a screw fit.

12. The seed holding device and shielding device of claim 1, wherein one of said inner and outer members defines a protrusion, wherein the other of said inner and outer members defines a recess adapted to receive said protrusion, and wherein said outer member is configured to slidably receive said inner member when said protrusion is inserted into said recess.

13. The seed holding device and shielding device of claim 1, wherein said inner member comprises a cantilever spring.

14. The seed holding device and shielding device of claim 13, wherein said cantilever spring defines a protrusion, and wherein said outer member defines a groove adapted to engage said protrusion.

15. The seed holding device and shielding device of claim 1, wherein said inner member and said outer member each comprise an exterior and an interior, wherein said inner member defines a first opening, wherein said outer member defines a second opening, and wherein when said inner and outer members are engaged with one another, there is no direct line of sight from the exterior of said outer member through said opening to the interior of said inner member.

* * * * *